US011150249B2

(12) United States Patent
Teramoto

(10) Patent No.: US 11,150,249 B2
(45) Date of Patent: Oct. 19, 2021

(54) MICROORGANISM IDENTIFICATION METHOD

(71) Applicant: SHIMADZU CORPORATION, Kyoto (JP)

(72) Inventor: Kanae Teramoto, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 16/801,162

(22) Filed: Feb. 26, 2020

(65) Prior Publication Data
US 2020/0300863 A1 Sep. 24, 2020

(30) Foreign Application Priority Data
Mar. 22, 2019 (JP) .............................. JP2019-055145

(51) Int. Cl.
G01N 33/00 (2006.01)
G01N 33/68 (2006.01)
H01J 49/00 (2006.01)
H01J 49/04 (2006.01)

(52) U.S. Cl.
CPC ...... *G01N 33/6851* (2013.01); *H01J 49/0036* (2013.01); *H01J 49/0418* (2013.01)

(58) Field of Classification Search
CPC ........... G01N 33/6851; G01N 2333/36; G01N 33/6848; H01J 49/0036; H01J 49/0418; C12Q 1/04
USPC .................................. 250/281, 282; 436/173
See application file for complete search history.

(56) References Cited

FOREIGN PATENT DOCUMENTS

| JP | 2006191922 | 7/2006 |
| JP | 2007316063 | 12/2007 |
| JP | 2015184020 | 10/2015 |

OTHER PUBLICATIONS

Teramoto, et al. ("Classification of Cutibacterium acnes at phylotype level by MALDI-MS proteotyping" Proc. Jpn. Acad. Ser. B. 95, 2019 (Year: 2019).*

Itaru Dekio et al., "Correlation between Phylogroups and Intracellular Proteomes of Propionibacterium acnes and Differences in the Protein Expression Profiles between Anaerobically and Aerobically Grown Cells," BioMed Research International, Jun. 26, 2013, pp. 1-10.

Itaru Dekio et al., "Dissecting the taxonomic heterogeneity within Propionibacterium acnes: proposal for *Propionibacterium acnes* subsp. acnes subsp. nov. and *Propionibacterium acnes* subsp. elongatum subsp. nov.," International Journal of Systematic and Evolutionary Microbiology, Sep. 30, 2015, pp. 4776-4787.

Elisabeth Nagy et al., "MALDI-TOF MS fingerprinting facilitates rapid discrimination of phylotypes I, II and III of Propionibacterium acnes," Anaerobe, Feb. 26, 2013, pp. 20-26.

(Continued)

*Primary Examiner* — Michael Maskell
(74) *Attorney, Agent, or Firm* — JCIPRNET

(57) ABSTRACT

A microorganism identification method utilizing mass spectrometry is provided. More specifically, a method for identifying a phylotype of *Cutibacterium acnes* utilizing mass spectrometry is provided. The method includes a) a step for reading out a m/z value of a peak derived from a marker protein on a mass spectrum which is obtained by mass spectrometry of a sample containing microorganisms; and b) a step for judging whether the sample contains *Cutibacterium acnes* (*C. acnes*) based on the m/z value.

16 Claims, 5 Drawing Sheets

(56) References Cited

OTHER PUBLICATIONS

Kanae Teramoto, et al., "Classification of Cutibacterium acnes at phylotype level by MALDI-MS proteotyping" Proc Jpn Acad Ser B Phys Biol Sci., vol. 95, Dec. 2019, pp. 612-623.
"Search Report of Europe Counterpart Application", dated Jul. 13, 2020, p. 1-p. 8.

* cited by examiner

| Protein | Phylotype | | | | | |
|---|---|---|---|---|---|---|
| | IA1 | IA2 | IB | II* | II** | III |
| L6 | 19706.6 | 19706.5 | 19706.5 | 19678.5 | 19678.5 | 19678.5 |
| | (9853.8) | (9853.8) | (9853.8) | (9839.8) | (9839.8) | (9839.8) |
| L13 | 16167.6 | 16167.6 | 16153.5 | 16167.6 | 16181.6 | 16153.5 |
| | (8084.3) | (8084.3) | (8077.3) | (8084.3) | (8091.3) | (8077.3) |
| L15 | 15384.7 | 15384.7 | 15384.7 | 15357.6 | 15357.6 | 15384.7 |
| | (7692.9) | (7692.9) | (7692.9) | (7679.3) | (7679.3) | (7692.9) |
| L23 | 11200.0 | 11200.0 | 11200.0 | 11200.0 | 11200.0 | 11181.0 |
| | (5600.5) | (5600.5) | (5600.5) | (5600.5) | (5600.5) | (5591.0) |
| Antitoxin | 7034.6 | 7004.5 | 7004.5 | 6985.5 | 6985.5 | 7004.5 |
| | (3517.8) | (3502.8) | (3502.8) | (3493.3) | (3493.3) | (3502.8) |

\* : Sequence types 42 and 46
\** : Sequence type 43
Numerical values in brackets ( ) show m/z values of divalent ion.

| Strains | | | Biomarkers | | | | | | | | |
| --- | --- | --- | --- | --- | --- | --- | --- | --- | --- | --- | --- |
| | | | L6 | | L13 | | | L15 | | L23 | | Antitoxin |
| Phylotype | ST* | JCM | 19678.6 | 19706.6 | 16153.5 | 16167.6 | 16181.6 | 15357.6 | 15384.7 | 11181.0 | 11200.0 | 7034.6 |
| IA1 | 6 | 6425 | 0 | 1 | 0 | 1 | 0 | 0 | 1 | 0 | 1 | 1 |
| | 6 | 6495 | 0 | 1 | 0 | 1 | 0 | 0 | 1 | 0 | 1 | 1 |
| | 6 | 18916 | 0 | 1 | 0 | 1 | 0 | 0 | 1 | 0 | 1 | 1 |
| | 6 | 18922 | 0 | 1 | 0 | 1 | 0 | 0 | 1 | 0 | 1 | 1 |
| | 6 | 18924 | 0 | 1 | 0 | 1 | 0 | 0 | 1 | 0 | 1 | 1 |
| IA2 | 9 | 18908 | 0 | 1 | 0 | 1 | 0 | 0 | 1 | 0 | 1 | 0 |
| | 9 | 18912 | 0 | 1 | 0 | 1 | 0 | 0 | 1 | 0 | 1 | 0 |
| | 22 | 18907 | 0 | 1 | 0 | 1 | 0 | 0 | 1 | 0 | 1 | 0 |
| | 22 | 18910 | 0 | 1 | 0 | 1 | 0 | 0 | 1 | 0 | 1 | 0 |
| IB | 10 | 18917 | 0 | 1 | 1 | 0 | 0 | 0 | 1 | 0 | 1 | 0 |
| | 10 | 18918 | 0 | 1 | 1 | 0 | 0 | 0 | 1 | 0 | 1 | 0 |
| | 10 | 18923 | 0 | 1 | 1 | 0 | 0 | 0 | 1 | 0 | 1 | 0 |
| | 10 | 18927 | 0 | 1 | 1 | 0 | 0 | 0 | 1 | 0 | 1 | 0 |
| II | | 6473 | 1 | 0 | 0 | 0 | 1 | 1 | 0 | 0 | 1 | 0 |
| | 42 | 18926 | 1 | 0 | 0 | 1 | 0 | 1 | 0 | 0 | 1 | 0 |
| | 43 | 18911 | 1 | 0 | 0 | 0 | 1 | 1 | 0 | 0 | 1 | 0 |
| | 43 | 18914 | 1 | 0 | 0 | 0 | 1 | 1 | 0 | 0 | 1 | 0 |
| | 43 | 18915 | 1 | 0 | 0 | 0 | 1 | 1 | 0 | 0 | 1 | 0 |
| | 43 | 18920 | 1 | 0 | 0 | 0 | 1 | 1 | 0 | 0 | 1 | 0 |
| | 43 | 18921 | 1 | 0 | 0 | 0 | 1 | 1 | 0 | 0 | 1 | 0 |
| | 46 | 18913 | 1 | 0 | 0 | 1 | 0 | 1 | 0 | 0 | 1 | 0 |
| III | 19 | 18909 | 1 | 0 | 1 | 0 | 0 | 0 | 1 | 1 | 0 | 0 |
| | 19 | 18919 | 1 | 0 | 1 | 0 | 0 | 0 | 1 | 1 | 0 | 0 |
| | 19 | 18925 | 1 | 0 | 1 | 0 | 0 | 0 | 1 | 1 | 0 | 0 |

*: Sequence type

FIG.5

MICROORGANISM IDENTIFICATION METHOD

CROSS-REFERENCE TO RELATED APPLICATION

This application claims the priority of Japan patent application serial no. 2019-055145, filed on Mar. 22, 2019. The entirety of the above-mentioned patent application is hereby incorporated by reference herein and made a part of this specification.

BACKGROUND

Technical Field

The disclosure relates to a microorganism identification method utilizing mass spectrometry. More specifically, the disclosure relates to a method for identifying a phylotype of *Cutibacterium acnes* utilizing mass spectrometry.

Related Art

As one of the methods for identifying the type of microorganism, a homology analysis based on DNA base sequences is conventionally known and is widely used in classification, verification and the like of microorganism (patent literature 1). In this method, first, DNA is extracted from a test microorganism to determine DNA base sequences of ribosome RNA genes and the like in regions existing in all organisms with high preservation. Next, the DNA base sequence is used to search a database in which multiple DNA base sequence data of known microorganisms is recorded, and a base sequence showing high similarity to the DNA base sequence of the test microorganism is selected out. Then, a judgment is made that an organism species from which the base sequence is derived is a species the same as or closely related to the test microorganism. However, in the method of utilizing DNA base sequence, it takes a relatively long time on DNA extraction from the test microorganism or determination of the DNA base sequence or the like, and thus there is a problem that a rapid microorganism verification is hard to perform. In addition, since an evolution rate of the ribosome RNA genes is relatively slow, comparison between organisms of markedly different systems is easy but comparison between extremely closely related species is generally difficult.

Therefore, in recent years, a method is used in which the microorganism verification is performed based on a mass spectrum pattern obtained by mass spectrometry of the test microorganism. According to the mass spectrometry, a tiny amount of microorganism samples can be used to obtain an analysis result in a short time and a continuous analysis of multiple specimens is also easy, and thus a simple and rapid microorganism verification can be achieved. In this method, first, a solution containing proteins extracted from the test microorganism, a suspension of the test microorganism and the like are analyzed by a mass spectrometry device using a soft ionization method such as MALDI-MS (Matrix Assisted Laser Desorption/Ionization Mass Spectrometry) or the like. Besides, the "soft" ionization method refers to an ionization method in which molecules that are easily decomposed by heat, such as proteins and synthetic polymers are resistant to decomposition. Then, the verification of the test microorganism is performed by matching the obtained mass spectrum pattern with the mass spectra patterns of multiple known microorganisms recorded in the database in advance. Because the mass spectrum pattern is utilized as microorganism-specific information (that is, fingerprint), this method is referred to as a fingerprint method (non-patent literatures 1 and 2).

In the microorganism verification using the above-described fingerprint method of the mass spectrometry, an identification at the level of subspecies, pathotype, strain or the like which is a lower classification level is generally difficult even though the verification at the species level can be made. Furthermore, in the fingerprint method, the protein from which each peak appearing on the mass spectrum is derived is not specified, and there is a problem on theoretical basis and reliability for verifying the microorganism. Therefore, in order to solve the problem, a method is developed in which utilizing the fact that about half of the peaks obtained by mass spectrometry of a microorganism fungus body is derived from ribosomal protein, a m/z value of the peaks obtained by mass spectrometry is associated with the mass estimated from an amino acid sequence which is obtained by translating the base sequence information of the ribosomal protein genes, and thereby the type of the proteins from which the peak is derived is attributed (patent literature 2). According to the method, a highly reliable microorganism verification based on theoretical basis can be performed.

Molecular weights of microbial proteins may vary, reflecting variations in the amino acid sequence of the protein depending on the taxonomy (family, genus, species, subspecies, pathotype, serotype, strain and the like). As a result, observed masses (m/z values) of the peaks in the mass spectrometry are different. Therefore, in order to perform discrimination at the pathotype or strain level with good reproducibility, it is important to select a marker peak that is used as a verification object and that can be utilized in the discrimination at the pathotype or strain level. For example, in patent literature 2, it is disclosed that 23 types of ribosome subunit proteins (L5, L13, L14, L15, L18, L19, L20, L22, L23, L24, L28, L30, L35, L36, S7, S8, S10, S13, S14, S17, S19, S20, and S21) can be utilized as a biomarker protein for discrimination and identifying *Pseudomonas putida* and related bacteria. In addition, in patent literature 3, it is disclosed that as a marker protein for discrimination and identifying pathotype *Escherichia coli* O157, O26 and O111 which are known as enterohemorrhagic *Escherichia coli* by mass spectrometry, a ribosomal protein S15, a ribosomal protein L25 and an acid stress chaperone HdeB can be utilized for O157, and a DNA binding protein H-NS can be utilized for O26 and O111.

[Patent literature 1] Japanese Laid-Open No. 2006-191922

[Patent literature 2] Japanese Laid-Open No. 2007-316063

[Patent literature 3] Japanese Laid-Open No. 2015-184020

[Non-patent literature 1] Dekio I, Culak R, Fang M, et al. Correlation between phylogroups and intracellular proteomes of *Propionibacterium acnes* and differences in the protein expression profiles between anaerobically and aerobically grown cells. Biomed Res Int. 2013; 2013: 151797.

[Non-patent literature 2] Dekio I, Culak R, Misra R, et al. Dissecting the taxonomic heterogeneity within *Propionibacterium acnes*: proposal for *Propionibacterium acnes* subsp. acnes subsp. nov. and *Propionibacterium acnes* subsp. elongatum subsp. nov. Int J Syst Evol Microbiol. 2015; 65: 4776-4787.

*Cutibacterium acnes* (*C. acnes*) is a gram-positive, anaerobic, and a normal skin bacteria. The *Cutibacterium acnes* keeps human skin in weakly acidic pH by producing propionic acid which inhibit the growth of pathogens on the skin. Furthermore, the *Cutibacterium acnes* is also reported to have an effect on producing antioxidant enzymes that work to inhibit skin inflammation caused by oxidative stress of ultraviolet rays and the like and protecting the skin (Allhorn M, et al. Sci Rep. 2016; 6: 36412). On the other hand, the *Cutibacterium acnes* is also known as a cause of acne vulgaris (acne) and the like. When sebum secretion increases in the skin, a hair follicle is closed by a keratotic plug, and comedones filled with sebum is formed in the hair follicle, the *Cutibacterium acnes* being anaerobic proliferates in the comedones, produces inflammatory substances and induces inflammation. Prevention of the *Cutibacterium acnes* infection causing osteomyelitis, endocarditis, endophthalmitis and the like, and resistance of a pollution to beauty equipment, artificial joint and medical instruments caused by the *Cutibacterium acnes*, it is necessary to rapidly analyze the phylotype of the *Cutibacterium acnes*.

The verification and classification of the *Cutibacterium acnes* are attempted by the above-described fingerprint method (non-patent literatures 1 and 2). The *Cutibacterium acnes* and reagents for ionization of the cytosolic components thereof are mixed on a vial or sample plate to prepare samples for analysis, the samples are analyzed by SALDI-MS (Surface Assisted Laser Desorption/Ionization Mass Spectrometry) or MALDI-MS (Matrix Assisted Laser Desorption/Ionization Mass Spectrometry), and a pattern of the mass spectrum or a pattern of the detected peaks around m/z of 7000-7300 vis used to identify and classify the *Cutibacterium acnes*. However, the mass spectrum of SALDI-MS in non-patent literature 1 is low in S/N ratio and lacks reliability. In non-patent literature 2, although SALDI-MS and MALDI-MS are used, the mass spectrum of SALDI-MS is low in S/N ratio and lacks reliability, and the peak used in classification is not identified to the specific protein and thus the basis for classification is not clear in MALDI-MS. Nagy E, et al. also report identification and classification of the *Cutibacterium acnes* performed by MALDI-MS, but the peak used in classification is not identified (Nagy E, et al. Anaerobe. 2013; 20: 20-26). Furthermore, in these methods using MALDI-MS, it is not successful to correctly classify the phylotype of the *Cutibacterium acnes* at present.

Therefore, in the current situation, a detailed analysis for identifying the phylotype of the *Cutibacterium acnes* is generally difficult, and the biomarker protein in which the peaks are separated and can be used in identification has not yet been specified in the mass spectrometry. Accordingly, a more reliable method for attributing the peak observed on the mass spectrum in the mass spectrometry is required.

SUMMARY

The disclosure is directed to an identification method of microorganism, in particular, *Cutibacterium acnes*, the identification method specifying and using a biomarker protein capable of reproducibly and rapidly identifying types I, II and III which are evolutionary lineage groups of the *Cutibacterium acnes*, and further identifying a phylotype constituting the type I.

The disclosure provides at least the following.

[1]

A microorganism identification method, including: a) a step for reading out a m/z value of a peak derived from a marker protein on a mass spectrum which is obtained by mass spectrometry of a sample containing microorganisms; and b) a step for judging whether the sample contains *Cutibacterium acnes* (*C. acnes*) based on the m/z value;

wherein the marker protein is one or more protein selected from a group consisting of ribosomal proteins L7/L12, L9, L18, L28, L29, L30, L31, S8, S15, S19 and S20.

[2]

A microorganism discrimination method, including: a) a step for reading out a m/z value of a peak derived from a marker protein on a mass spectrum which is obtained by mass spectrometry of a test microorganism; and b) a step for judging whether the test microorganism is a *C. acnes* type I, II or III based on the m/z value;

wherein the marker protein is a combination of ribosomal proteins L6 and L23, a combination of ribosomal proteins L15 and L23, or a combination of ribosomal proteins L6 and L15.

[3]

A microorganism identification method, including: a) a step for reading out a m/z value of a peak derived from a marker protein on a mass spectrum which is obtained by mass spectrometry of a test microorganism; and b) a step for judging whether the test microorganism is a phylotype IA1, IA2 or IB of a *C. acnes* type I based on the m/z value; wherein the marker protein is a combination of a ribosomal protein L13 and an antitoxin.

[4]

The discrimination method according to [3], wherein the m/z value of the peak of the antitoxin on the mass spectrum is 7034.6.

[5]

The discrimination method according to any one of [1] to [4], wherein the marker protein on the mass spectrum further includes double charged ions.

[6]

A microorganism discrimination method, including: a) a step for reading out a m/z value of a peak derived from a marker protein on a mass spectrum which is obtained by mass spectrometry of a sample containing microorganisms, and b) a step for judging whether the sample includes at least one of a *C. acnes* type I, II or III based on the m/z value;

wherein in the step b), on the mass spectrum, in regard to a combination of ribosomal proteins L6 and L23, a combination of ribosomal proteins L15 and L23, or a combination of ribosomal proteins L6 and L15, when there is at least one peak which reflecting specific mutation in the amino-acid sequence for I, II, and III, it is judged that the sample comprises at least one of the *C. acnes* type I, II or III.

[7]

A program for making a computer execute each step according to any one of [1] to [6].

[8]

An analysis method of skin bacterial flora using the identification method according to any one of [1] to [6].

BRIEF DESCRIPTION OF THE DRAWINGS

FIG. 5 is a diagram showing a peak profile for *C. acnes* proteo-typing. Sequence type is a classification based on Multilocus Sequence Typing (MLST).

DESCRIPTION OF THE EMBODIMENTS

According to the disclosure, a discrimination can be reproducibly and rapidly made on whether the sample contains the *Cutibacterium acnes* (*C. acnes*) which is a representative skin resident bacteria, and on whether the test microorganism is *C. acnes* type I, II or III. Furthermore, according to the disclosure, a subtype IA1, IA2 or IB of the *C. acnes* type I can be reproducibly and rapidly identified.

Although the *C. acnes* is involved in the induction of skin diseases such as acne and the like and skin inflammations, it is considered that the skin diseases and skin inflammations are mainly caused by the *C. acnes* type I. According to the disclosure, the *C. acnes* type I in the sample can be rapidly and simply identified, and thus a skin bacterial flora analysis that is important for treatment or prevention of the skin diseases such as acne and the like can be rapidly and simply performed. Furthermore, according to the disclosure, a skin condition evaluation based on the skin bacterial flora analysis can be simply performed, and thus an evaluation of skin care can be easily performed.

Figure 1:
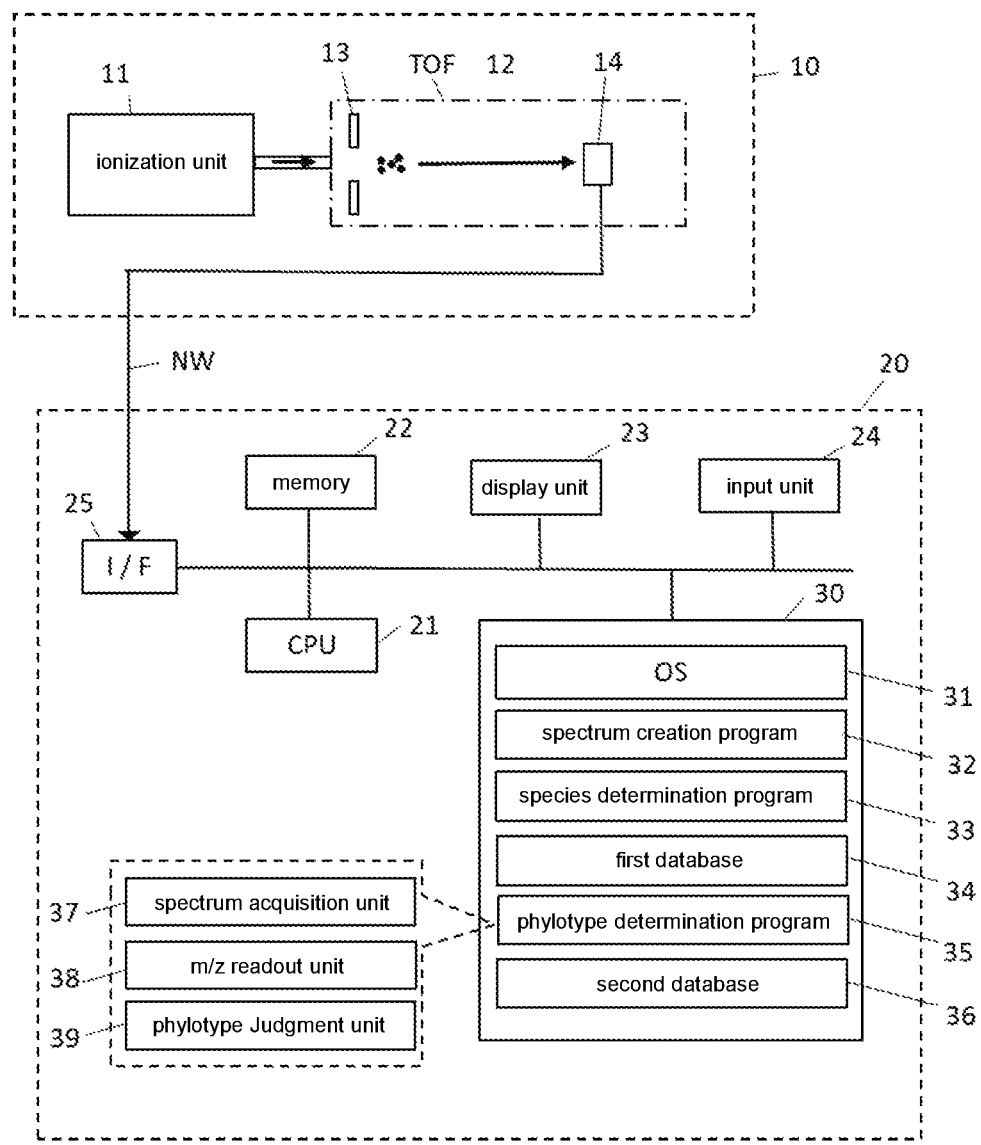
FIG. 1 is an overall view of a microorganism discrimination system used in a microorganism discrimination method of the disclosure.

FIG. 1 is an overall view of a microorganism discrimination system used in a microorganism identification method of the disclosure.

The microorganism discrimination system roughly consists of a mass spectrometry unit 10 and a microorganism discrimination unit 20. The mass spectrometry unit 10 includes an ionization unit 11 which ionizes molecules and atoms in a sample by matrix assisted laser desorption/ionization mass spectrometry (MALDI), and a time-of-flight mass separator (TOF) 12 which separates various ions emitted from the ionization unit 11 corresponding to a m/z value.

The TOF 12 includes an extraction electrode 13 by which the ions are extracted from the ionization unit 11 and guided to an ion flight space in the TOF 12, and a detector 14 which detects the ions mass separated in the ion flight space.

The entity of the microorganism discrimination unit 20 is a computer such as a workstation, a personal computer and the like; a display unit 23 consisting of a memory 22, a LCD (Liquid Crystal Display) and the like, an input unit 24 consisting of a keyboard, a mouse and the like, and a storage unit 30 consisting of a large-capacity storage device such as a hard disk, a SSD (Solid State Drive) and the like are connected to each other in a CPU (Central Processing Unit) 21 which is a central operation processing device. In the storage unit 30, an OS (Operating System) 31, a spectrum creation program 32, a species determination program 33, and a phylotype determination program 35 (the program of the disclosure) are stored, and a first database 34 and a second database 36 are stored. The microorganism discrimination unit 20 further includes an interface (I/F) 25 for managing a direct connection to external devices and a connection to external devices and the like via a network such as LAN (Local Area Network) and the like, and is connected from the interface 25 to the mass spectrometry unit 10 via a network cable NW (or wireless LAN).

In FIG. 1, a spectrum acquisition unit 37, a m/z readout unit 38, and a phylotype judgment unit 39 are shown as being related to the phylotype determination program 35 (the program of the disclosure). Any one of these units is basically a functional part implemented by software by the CPU 21 executing the phylotype determination program 35. Besides, the phylotype determination program 35 is not necessarily an independent program; for example, the phylotype determination program 35 may be a function incorporated into the species determination program 33 or a part of a program for controlling the mass spectrometry unit 10, and the form of the phylotype determination program 35 is not particularly limited.

In addition, in FIG. 1, the spectrum creation program 32, the species determination program 33, the phylotype determination program 35, the first database 34, and the second database 36 are mounted on a terminal operated by a user; however, at least a part or all of these programs and databases may be arranged in another device connected to the terminal by a computer network, and processing performed by the programs arranged in the another device and/or an access to the databases are/is executed according to instructions from the terminal.

In the first database 34 of the storage unit 30, multiple mass lists related to the known microorganisms are registered. The mass list enumerates m/z values of detected peaks in mass spectra from some microorganism cells. The mass list includes information of the m/z values, taxonomic information (family, genus, species, and the like) of the microorganism. This mass list is desirably created based on data obtained from various microorganisms' cells using the same ionization method and mass separation method as the method performed by the mass spectrometry unit 10.

When the mass list is created from the actually measured data, first, peaks that appear in a prescribed m/z value range are extracted from the mass spectrum acquired as the actually measured data. At this time, the peaks mainly derived from proteins can be extracted by setting the m/z value range to about 3,000-20,000. In addition, undesired peaks (noises) can be excluded by extracting only the peaks of which the peak height (relative intensity) is above a prescribed threshold. Besides, large amount of ribosomal protein groups are expressed in the cells, and thus most of the m/z values described in the mass list can be made to be derived from the ribosomal protein by properly setting the threshold. Then, the m/z value (m/z) of the peaks extracted as described above is listed for each cell, and is registered in the first database 34 after the classification information and the like are added. Besides, desirably, the culture environment is standardized in advance for each microorganism cell used in collection of the actually measured data so as to suppress variations in gene expression caused by culture conditions.

In the second database 36 of the storage unit 30, information related to a marker protein for identifying the known microorganisms by a classification (subspecies, pathotype, serotype, strain and the like) more detail than species is registered. The information related to the marker protein at least includes information of the m/z value (m/z) of the marker protein in the known microorganisms. The marker protein stored in the second database 36 may be a divalent ion. Besides, the m/z value (m/z) described in the specification is a value for monovalent ions unless otherwise stated. In the second database 36 of the embodiment, at least the values of m/z values respectively corresponding to the ribosomal proteins L7/L12, L9, L18, L28, L29, L30, L31, S8, S15, S19 and S20 (L7/L12: m/z 13571.4, L9: m/z 16118.8, L18: m/z 13570.6, L28: m/z 6807.0, L29: m/z 8754.9, L30: m/z 6786.9, L31: m/z 7718.8, S8: m/z 14525.7, S15: m/z 10080.7, S19: m/z 10380.0 and S20: m/z 9570.0)

are stored to identify *C. acnes* strains. Furthermore, in the second database 36, the marker proteins L6, L15 and L23 (L6: m/z 19678.5 or m/z 19706.6, L15: m/z 15384.7 or m/z 15357.6, and L23: m/z 11181.0 or m/z 11200.0) are registered to identify *C. acnes* type I, II, and III. Here, the information related to the marker proteins L6, L15 and L23 for identifying the type I is L6: m/z 19706.6 and L23: m/z 11200.0, L15: m/z 15384.7 and L23: m/z 11200.0, or L6: m/z 19706.6 and L15: m/z 15384.7. The information related to the marker proteins L6, L15 and L23 for identify the type II is L6: m/z 19678.6 and L23: m/z 11200.0, L15: m/z 15357.6 and L23: m/z 11200.0, or L6: m/z 19678.6 and L15: m/z 15357.6. The information related to the marker proteins L6, L15 and L23 for identify the type III is L6: m/z 19678.6 and L23: m/z 11181.0, L15: m/z 15384.7 and L23: m/z 11181.0, or L6: m/z 19678.6 and L15: m/z 15384.7.

Furthermore, in the second database 36, the marker proteins L6, L15 and L23 (L6: m/z 19678.5 or m/z 19706.6, L15: m/z 15384.7 or m/z 15357.6, and L23: m/z 11181.0 or m/z 11200.0) are registered to identify *C. acnes* type I, II, and III. Furthermore, in the second database 36, the m/z values (m/z 16153.5, m/z 16167.6 and m/z 16180.7) corresponding to L13 and m/z 7034.6 corresponding to an antitoxin of the *C. acnes* are registered as the marker protein for subdividing the *C. acnes* type I into the subtypes IA1, IA2 and IB. The antitoxin means an antitoxic protein coded into chromosome or plasmid DNA of a bacterium. Here, for the information related to the marker protein for subdividing the *C. acnes* type I into the subtype IA1, L13 is m/z 16167.6 and antitoxin is m/z 7034.6. The marker proteins for subdividing the *C. acnes* type I into the subtype IA1 are L13 (m/z 16167.6) and antitoxin (m/z 7034.6). *C. acnes* subtype IA2 is subdivided from type I with L13 (m/z 16167.6). Here, the antitoxin in subtype IA2 is not detected at m/z 7034.6. *C. acnes* subtype IB is subdivided from type I with L13 (m/z 16153.6). Here, the antitoxin in subtype IB is not detected at m/z 7034.6.

Desirably, detected m/z values are compared with the theoretical masses calculated from amino-acid sequence of each marker protein. The marker proteins whose detected masses and calculated masses are matched and selected as the marker proteins stored in the second database 36. As the amino-acid sequence of each marker protein, an amino-acid sequence translated from DNA sequence or an amino-acid sequence registered in a protein DB can be used. In addition, the DNA sequences registered in a public database, for example, the database of NCBI (National Center for Biotechnology Information) can also be used. It is desirable to consider a cleavage of N-terminal methionine residues as a post-translational modification when calculate the theoretical masses from the amino-acid sequences. Specifically, when the second amino-acid residue from the N-terminal is glycine, alanine, serine, proline, valine, threonine or cysteine, the theoretical value is calculated regarding the marker protein as a protein in which the N-terminal methionine is cleaved. In addition, since detected protein ions by MALDI-TOF MS are protonated molecules, mass of proton should be considered in calculating of theoretical masses.

Figure 2:
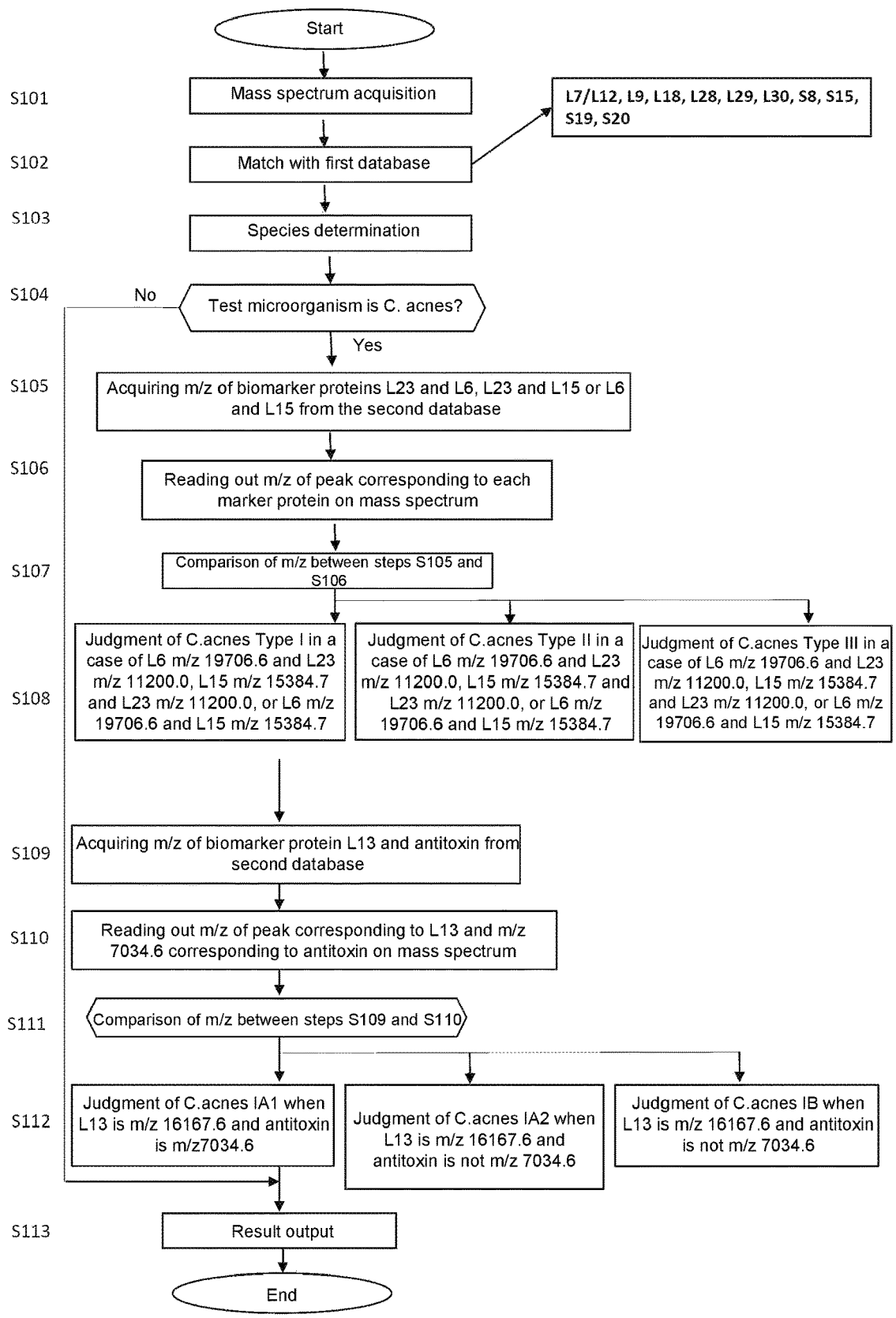
FIG. 2 is a diagram showing a *C. acnes* type discrimination procedure using the microorganism discrimination method of the disclosure.

An identification procedure of the *C. acnes* types I, II and III using the microorganism identification system of the embodiment is described with reference to a flowchart (FIG. 2).

First, the user prepares a sample containing components of the test microorganism, and sets the sample in the mass spectrometry unit 10 to execute mass spectrometry. In this case, a fungus body or cell suspension can be directly used as the sample. However, preferably a cell extract is used, and more preferably a sample obtained by concentration or purification of cell components of the ribosomal protein and the like from the cell extract is used.

The spectrum creation program 32 acquires, via the interface 25, a detection signal obtained from the detector 14 of the mass spectrometry unit 10, and creates the mass spectrum of the test microorganism based on the detection signal (step S101).

Next, the species determination program 33 matches the mass spectrum of the test microorganism with the mass list of the known microorganisms recorded in the first database 34, and extracts the mass list of the known microorganisms having a m/z value pattern similar to the mass spectrum of the test microorganism, for example, a mass list in which many peaks are consistent with the respective peaks in the mass spectrum of the test microorganism in a prescribed error range (preferably 50-500 ppm, more preferably 150-200 ppm) (step S102). Subsequently, the species determination program 33 specifies, by referring to the classification information stored in the first database 34 in association with the mass list extracted in step S102, an organism species to which the known microorganism corresponding to the mass list belongs (step S103). Then, when the organism species is not *C. acnes* ("No" in step S104), the organism species is output to the display unit 23 as the organism species of the test microorganism (step S113), and the identification processing ends. On the other hand, when the organism species is *C. acnes* ("Yes" in step S104), the procedure subsequently proceeds to identification processing performed by the phylotype determination program 35. Besides, when it is judged that the sample contains the *C. acnes* by other methods in advance, the procedure may proceed to the phylotype determination program 35 without utilizing the species determination program using the mass spectrum.

In the phylotype determination program 35, first, the phylotype judgment unit 39 respectively reads out the values of m/z values of the antitoxin and the ribosomal proteins L6, L13, L15, L23 which are marker proteins from the second database 36 (step S105). Subsequently, the spectrum acquisition unit 37 acquires the mass spectrum of the test microorganism created in step S101. Then, the m/z value readout unit 38 selects, on the mass spectrum, the peak that appears in a m/z value range stored in the second database 36 in association with each of the marker proteins as the peak corresponding to each marker protein, and reads out the m/z value thereof (step S106). After that, the phylotype judgment unit 39 compares the m/z value and the value of m/z value of each marker protein read out from the second database 36, and judges whether the two are consistent within a prescribed allowable error range (step S107). When the two are consistent as a result, it is judged that the test microorganism is any one of the *C. acnes* types I, II or III (step S108), and the fact is output to the display unit 23 as an identification result of the test microorganism (step S113).

Furthermore, the *C. acnes* classified as the type I in step S108 can be subdivided into the subtype IA1, IA2, or IB by reading out the value of m/z value of L13 and the m/z 7034.6 corresponding to the antitoxin (steps S111 and S112). Besides, when it is judged that the sample includes the *C. acnes* type I by other methods in advance, the *C. acnes* type I can be further subdivided into the subtype IA1, IA2, or IB by executing steps S111 and S112 only.

The embodiment of the disclosure is described above with reference to the drawings, but the disclosure is not limited to the above embodiment, and appropriate changes are allowed within the scope of the disclosure.

EXAMPLES

A selection procedure of the marker proteins in the disclosure and an experiment conducted to demonstrate the effect of the disclosure are described below, but the scope of the disclosure is not limited hereto.

(1) Strain and Culture Condition 22 strains of the *C. acnes* are used to construct a protein mass database. These strains are purchased from Japan Collection of Microorganisms (JCM) of Bioresource Research Center in Institute of Physical and Chemical Research (Tsukuba City, Japan). A modified GAM medium or a GAM medium of Nissui Pharmaceutical CO., LTD. is used in cultivation of the *C. acnes*.

(2) Construction of Protein Mass Database

An amino acid sequence of ribosomal subunit protein is obtained from the database of National Center for Biotechnology Information (NCBI) in the U.S. Compute pI/Mw tool of ExPASy proteomics server provided by Swiss Institute of Bioinformatics is used in calculation of the calculation mass of each protein. At this time, when the second amino acid residue from the N-terminal is glycine, alanine, serine, proline, valine, threonine or cysteine, the calculation mass is calculated regarding the protein as a protein in which the N-terminal Methionine is cleaved.

(3) Measurement Using MALDI-TOF MS

Bacterial cells on an agar medium or fungus recycled from a liquid medium by centrifugation are used in measurement. The bacterial cells are suspended with distilled water (OD610=1). The bacterial cell suspension (500 μL) is crushed using bead-beating at 5000 rpm three times at 60 seconds each. Crushed bacterial cell is centrifuged to remove debris (15000 g, 5 minutes), and a cell-lysate is obtained as a supernatant. Ribosomal fraction is obtained by ultrafiltration (Nominal molecular weight limit: 30 kDa, 14000 g, 10 minutes) as a captured fraction. Sinapinic acid (SA) or α-cyano-4-hydroxycinnamic acid (CHCA) is used as a matrix reagent. SA or CHCA matrix solution at a concentration of 15 mg/mL in 50% acetonitrile (ACN) with 1% trifluoroacetic acid (TFA) is used for MALDI-MS sample preparation. 10 μl of matrix solution is mixed with 1 μL of ribosome fraction, and 1 μL of the mixture is dropped on a sample plate and air dried.

The MALDI-MS measurements are performed using an AXIMA Performance™ mass spectrometer in the positive ion linear mode. The assignment of detected peaks is judged from mass differences within 200 ppm compared between the calculated masses as $[M+H]^+$ ions and the detected masses in the MALDI mass spectra.

Each of following ribosomal protein, L7/L12, L9, L18, L28, L29, L30, L31, S8, S15, S19 and S20, are clearly detected from all the sample strains at the same m/z values.

Figures 3, 4:
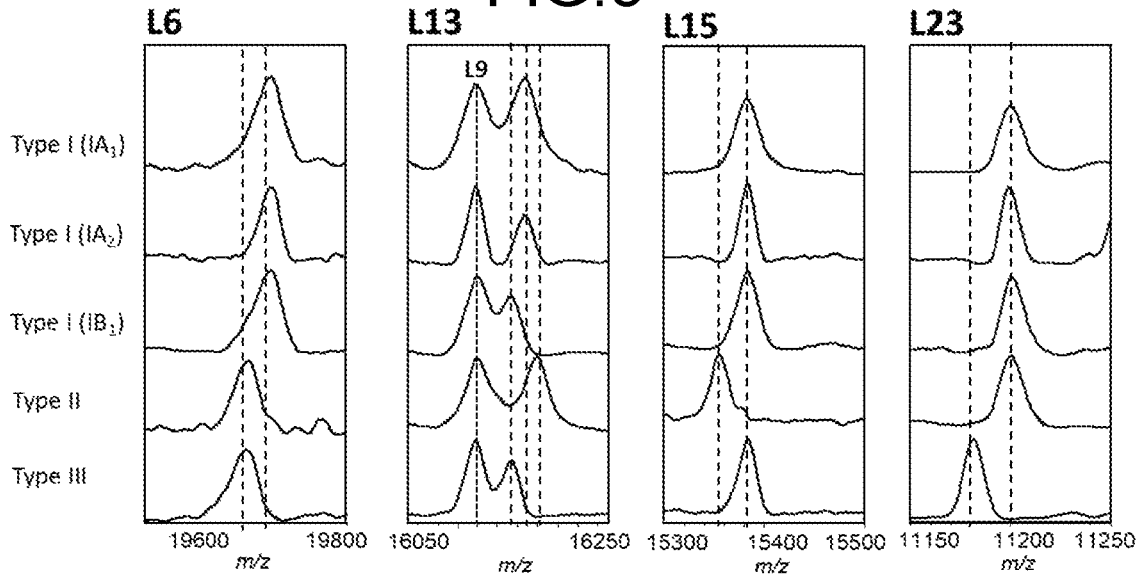
FIG. 3 is a list of marker proteins for *C. acnes* typing. Sequence type is a classification based on Multilocus Sequence Typing (MLST).
FIG. 4 is a diagram showing peaks on a mass spectrum contributing to the *C. acnes* typing.

Detected m/z values of biomarker proteins which contribute to the phylotype identification are shown in FIG. 3 and FIG. 4. The following is shown based on FIG. 3 and FIG. 4.

By focusing on L23, the type III can be discriminated (type III: m/z 11180.9, types I and II: m/z 11200.0).

By focusing on L15, the type II can be discriminated (type II: m/z 15357.6, types I and III: m/z 15384.7).

By focusing on L6, the type I can be discriminated (type I: m/z 19706.6, types II and III: m/z 19678.5).

By focusing on L13, the phylotype IB of the type I can be discriminated (IB: m/z 16153.5, IA1 and IA2: m/z 16167.6).

By focusing on the peak (antitoxin) of m/z 7034.6, the IA1 of the type I can be discriminated.

By focusing on L13 and the peak (antitoxin) of m/z 7034.6, the IA1 or IA2 and IB of the type I can be discriminated.

(4) Cluster Analysis

Figure 6:
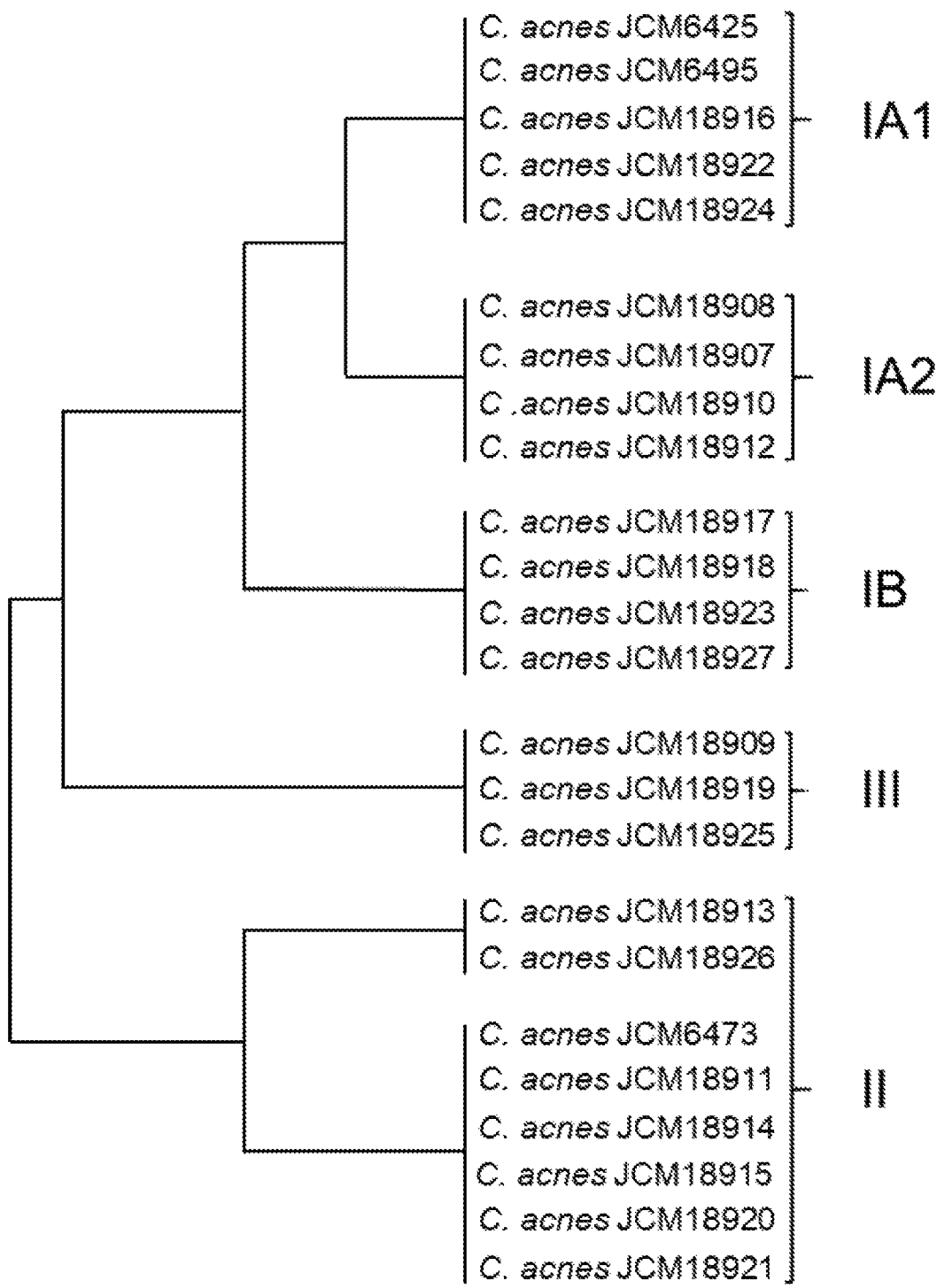
FIG. 6 is a dendrogram showing a classification result of the *C. acnes*.

All the sample strains are confirmed as *C. acnes* by MALDI-MS. The judgement results for each biomarker protein are summarized in the table, in which scores used either 1 or 0 (FIG. 5). "1" means that a biomarker peak is detected, and "0" means that biomarker peak is not detected. The data is used for cluster analysis to create a dendrogram (FIG. 6). As shown in FIG. 6, *C. acnes* strains are successfully classified into the types I, II and III. Furthermore, the type I related to skin inflammation can be further divided into subtype IA1, IA2 and IB. Accordingly, an analysis method of skin bacterial flora is provided.

What is claimed is:

1. A microorganism identification method, comprising:
   a) a step for reading out a m/z value of a peak derived from a marker protein on a mass spectrum, which is obtained by mass spectrometry of a sample containing microorganisms; and
   b) a step for judging whether the sample contains *Cutibacterium acnes* (*C. acnes*) based on the m/z value;
   wherein the marker protein is one or more proteins selected from a group consisting of ribosomal proteins L7/L12, L9, L18, L28, L29, L30, L31, S8, S15, S19 and S20.

2. A microorganism identification method, comprising:
   a) a step for reading out a m/z value of a peak derived from a marker protein on a mass spectrum, which is obtained by mass spectrometry of a test microorganism; and
   b) a step for judging whether the test microorganism is a *C. acnes* type I, II or III based on the m/z value;
   wherein the marker protein is a combination of ribosomal proteins L6 and L23, a combination of ribosomal proteins L15 and L23, or a combination of ribosomal proteins L6 and L15.

3. A microorganism identification method, comprising:
   a) a step for reading out a m/z value of a peak derived from a marker protein on a mass spectrum, which is obtained by mass spectrometry of a test microorganism; and
   b) a step for judging whether the test microorganism is a phylotype IA1, IA2 or IB of a *C. acnes* type I based on the m/z value;
   wherein the marker protein is a combination of a ribosomal protein L13 and an antitoxin.

4. The identification method according to claim 3, wherein the m/z value (m/z) of the peak of the antitoxin on the mass spectrum is 7034.6.

5. The identification method according to claim 1, wherein the marker protein on the mass spectrum further comprises a divalent ion.

6. The identification method according to claim 2, wherein the marker protein on the mass spectrum further comprises a divalent ion.

7. The identification method according to claim 3, wherein the marker protein on the mass spectrum further comprises a divalent ion.

8. A microorganism identification method, comprising:
   a) a step for reading out a m/z value of a peak derived from a marker protein on a mass spectrum, which is obtained by mass spectrometry of a sample containing microorganisms, and b) a step for judging whether the sample comprises at least one of a *C. acnes* type I, II or III based on the m/z value;

wherein in the step b), on the mass spectrum, in regard to a combination of ribosomal proteins L6 and L23, a combination of ribosomal proteins L15 and L23, or a combination of ribosomal proteins L6 and L15, when there is at least one peak of a m/z value in a case of having mutations specific to the *C. acnes* types I, II, and III, it is judged that the sample comprises at least one of the *C. acnes* type I, II or III.

9. A program for making a computer execute each step according to claim 1.

10. A program for making a computer execute each step according to claim 2.

11. A program for making a computer execute each step according to claim 3.

12. A program for making a computer execute each step according to claim 8.

13. An analysis method of skin bacterial flora using the identification method according to claim 1.

14. An analysis method of skin bacterial flora using the identification method according to claim 2.

15. An analysis method of skin bacterial flora using the identification method according to claim 3.

16. An analysis method of skin bacterial flora using the identification method according to claim 8.

* * * * *